(12) United States Patent
Castillo Nara

(10) Patent No.: US 8,372,391 B2
(45) Date of Patent: Feb. 12, 2013

(54) BIOFUNGICIDAL COMPOSITION FOR CONTROLLING PHYTOPATHOGENIC FUNGI

(75) Inventor: Antonio Castillo Nara, Santiago (CL)

(73) Assignee: Universidad de Santiago de Chile, Santiago (CL)

( * ) Notice: Subject to any disclaimer, the term of this patent is extended or adjusted under 35 U.S.C. 154(b) by 0 days.

(21) Appl. No.: 13/264,406

(22) PCT Filed: Jun. 16, 2010

(86) PCT No.: PCT/CL2010/000023
§ 371 (c)(1),
(2), (4) Date: Jan. 6, 2012

(87) PCT Pub. No.: WO2010/118548
PCT Pub. Date: Oct. 21, 2010

(65) Prior Publication Data
US 2012/0107280 A1    May 3, 2012

(30) Foreign Application Priority Data

Apr. 16, 2009   (CL) .................................... 908-2009

(51) Int. Cl.
*A01N 63/00* (2006.01)
*A01P 3/00* (2006.01)
*C12N 1/20* (2006.01)

(52) U.S. Cl. .................................. 424/93.4; 435/252.1

(58) Field of Classification Search ................. 424/93.1
See application file for complete search history.

(56) References Cited

U.S. PATENT DOCUMENTS

| | | | | |
|---|---|---|---|---|
| 5,597,565 A | * | 1/1997 | Leifert et al. | 424/115 |
| 5,780,080 A | * | 7/1998 | Leifert et al. | 426/49 |
| 5,869,038 A | | 2/1999 | Leifert et al. | |

FOREIGN PATENT DOCUMENTS

| | | | |
|---|---|---|---|
| WO | 01/40442 | A1 | 6/2001 |
| WO | 02072795 | A2 | 9/2002 |

OTHER PUBLICATIONS

Kamensky et al., Soil-borne strain IC14 of *Serratia plymuthica* with multiple mechanisms of antifungal activity provides biocontrol of *Botrytis cinerea* and *Sclerotinia sclerotiorum* diseases, Soil Biology and Biochemistry, vol. 35, Issue 2, Feb. 1, 2003, pp. 323-331.*
Meziane et al., Control of green and blue mould on orange fruit by *Serratia plymuthica* strains IC14 and IC1270 and putative modes of action, Postharvest Biology and Technology, vol. 39, Issue 2, Feb. 2006, pp. 125-133.*
International Search Report—PCT/CL2010/000023—Dated Nov. 8, 2010 (3 pages).
Yandong Pang et al., "Induction of systemic resistance, root colonisation and biocontrol activies of the rhizospheric strain of *Serratia plymuthica* are dependent on N-acyl homoserine lactones," Eur. J. Pathol., 124:261-268 (2009).
Jun'ichi Shoji et al., "Isolation of CB-25-I, An Antifungal Antibiotic, From *Serratia plymuthica*," The Journal of Antibiotics, vol. XLII, No. 6, pp. 869-874 (1989).
Marco Kai et al., "Volatiles of bacterial antagonists inhibit mycelial growth of the plant pathogen *Rhizoctonia solani*," Archives of Microbiology, 187:351-360 (2007).
Jan A.L. van Kan, "Licensed to kill: the lifestyle of a necrotrophic plant pathogen," Trends in Plant Science, vol. 11, No. 5, pp. 247-253 (2006).

* cited by examiner

*Primary Examiner* — Karen Cochrane Carlson
*Assistant Examiner* — Jennifer M. H. Tichy
(74) *Attorney, Agent, or Firm* — Abelman, Frayne & Schwab

(57) ABSTRACT

Biofungicide composition derived from a biologically pure culture of a Chilean bacterial isolate obtained from the skin of grapes, corresponding to *Serratia plymuthica* CCGG2742, to be used as an environmentally friendly biological control agent against fungal diseases of vegetables, in particular fruits susceptible to the infection of *Botrytis cinerea*, efficiently preventing the germination of conidia and the proliferation of mycelia of said phytopathogenic fungus, furthermore protecting the plant's leaves and fruits from the infection by the same fungus, and having the potential of being used in the biological control of other phytopathogenic fungus and microorganisms.

10 Claims, 8 Drawing Sheets

```
TTTTTATGACGCTGGCGGCAGGCCTAACACATGCAAGTCGAGCGGTAGCACAGGAGAGCTTGCTCTCCGGGTG
ACGAGCGGCGGACGGGTGAGTAATGTCTGGGAAACTGCCTGATGGAGGGGGATAACTACTGGAAACGGTAGCT
AATACCGCATAACGTCTACGGACCAAAGTGGGGGACCTTCGGGCCTCACGCCATCAGATGTGCCCAGATGGGA
TTAGCTAGTAGGTGGGGTAATGGCTCACCTAGGCGACGATCCCTAGCTGGTCTGAGAGGATGACCAGCCACAC
TGGAACTGAGACACGGTCCAGACTCCTACGGGAGGCAGCAGTGGGGAATATTGCACAATGGGCGCAAGCCTGA
TGCAGCCATGCCGCGTGTGTGAAGAAGGCCTTAGGGTTGTAAAGCACTTTCAGCGAGGAGGAAGGGTTCAGTG
TTAATAGCACTGTGCATTGACGTTACTCGCAGAAGAGCACCGGCTAACTCCGTGCCAGCAGCCGCGGTAATAC
TGATGGTGCAAGCGTTAATCGGAATTACTGGGCGTAAAGCGCACGCATGCGGTTTGTTAAGTCAGATGTGAAA
TCCCCGCGCTTAACGTGAGAACTGCATTTGAAACTGTAAACTAGATTCTTGTAGAGGGGGGTAAAAATCTCAG
TGTTTCTGTCAAAGTCTTTCAATCTGCACTTATCCCTACGCATAAGCTGCTTCTGTTACAATTCTGACCTACA
TTGTAATTTCGACGTATAAACTTATTATTATCTTGGTCTCTCGCGTTACTCTAGTGATTAGATTTGTCTATTA
TTCTTGTTCTCAAGTATTGTTTCTATATACTTTTTATCTTCCAATCCTTCGGTTACCTTTATATTTTATTCCC
TTCTCTTTTCACATAACTGCTATATTGTATTTCATTTTCTTCATTTCTTTAACTTCACATTCTTTGTCCTTTG
TTACCTCTTTCAAAATATTCTTCCGTTAATGAGTTCTCCAGTAGC
```

BIOFUNGICIDAL COMPOSITION FOR CONTROLLING PHYTOPATHOGENIC FUNGI

RELATED APPLICATIONS

This application is a §371 of PCT/CL2010/000023 filed Jun. 16, 2010, and claims priority from Chilean Patent Application No. 908-2009 filed Apr. 16, 2009, both incorporated by reference in their entirety.

FIELD OF THE INVENTION

The present invention relates to fungitoxic bacteria, specifically the wild-type strain *Serratia plymuthica* CCGG2742 and the fungitoxic molecules that it secretes, as agents for the biologic control of phytopathogenic fungi, in particular the *Botrytis cinerea* fungus, that causes fruit grey rooting pre and post harvest. The bacteria can be used as a living organism both before and after the harvest, since is a wild saprophyte microorganism that does not show pathogenicity neither to animals nor to plants. Also it is possible to use a concentrate of the secreted molecules or preparations of the pure fungitoxic molecules in individual form.

SUMMARY OF THE INVENTION

This inventions relates to the provision of a wild-type bacterial strain, characterized as *Serratia plymuthica* CCGG2742 and its use as a biofungicide. Said bacterial strain has been deposited in the Spanish Culture Type Collection (Colección Española de Cultivos Tipo, CECT), University of Valencia, Spain in accordance with the Budapest Treaty on Nov. 7, 2008. The accession number assigned by the international deposit authority is CECT 7404. This wild-type bacteria, originally of Chile, was isolated from grapes skin and has the capacity of killing different isolates and wild-type strains of the phytopathogenic fungus *B. cinerea*. The fungicide capacity of the bacteria is due to the secretion of fungitoxic molecules that interact with the fungi, resulting in its destruction, and therefore inhibiting the germination of the conidia, and the fungal mycelia proliferation.

Many of the bio-fungicides currently in use are particularly pathogenic for the human being and for plants. On the contrary, *Serratia plymuthica* CCGG2742 is not pathogenic nor toxic to plants or fruits, and it has also been informed that it wouldn't be pathogenic to animals nor to humans. Experiments conducted in the laboratory reveal that its inoculation in bean and grapevine plants leaves does not result in any visible alteration of these hosts, as observed days after the inoculation at 20° C., in dishes that contained only 1.5% (w/v) agar-agar in order to maintain the humidity at a suitable level. In the same way, when a high level of inoculum of the bacterial strain is added ($2\times10^{10}$ cfu (colony forming units)/grape berry) to healthy or wounded grapes, no effect is seen after 7 days of incubation in the same conditions as describe before. Another problem with current bacterial biofungicides is its low survival time in the plants and fruits surface that are to be protected from the attack of phytopathogenic fungi. Experiments conducted in the laboratory reveal that the CCGG2742 strain inoculated on grapes, in doses in the range of $10^6$-$10^8$ cfu/cm$^2$, reaches levels of $10^3$-$10^5$ cfu/cm$^2$ on the fruit's skin surface, and if the grapes have wounds, the bacterial populations grows to $10^3$-$10^7$ cfu/cm$^2$ 24 hours after the inoculation at 20° C., maintaining the same level for 5-7 days when the fruit is stored at 4° C., protecting it from the *B. cinerea* infection.

The biological agent of the invention corresponds to a wild bacteria, isolated from the field, that is generally on the skin of grapes and that has been identified my means of biochemical, microbiological, electron microscopy and 16S rDNA sequencing techniques. *S. plymuthica* CCGG2742 is a Chilean originally strain and corresponds to a saprophyte organism, not pathogenic to plants nor animals, and therefore its living cells are suitable to be used as a biofungicide against *B. cinerea*.

Furthermore, the present invention relates to compositions that contain said bacterial strain or extracts that contain the same, or to solutions or mixtures that contain compounds derived therefrom (for example, fungitoxic molecules secreted by said bacterial strain), all of them capable of protecting the plants and their fruits from the attack of phytopathogenic microorganisms during the periods of pre and post harvest.

The present invention also includes any mutant derived from the wild-type strain that possesses essentially the same characteristics.

In the same way, the invention relates to the procedure for obtaining said bacterial strain or its derivatives and to the applications of the same in the protection of plants, especially of fruits.

Even more, the present invention provides a formulation to control fungal diseases in plants using the pure *Serratia plymuthica* CCGG2742 bacterial strain. The use of this bacteria constitutes a natural alternative for the chemically synthesized fungicides, thereby warranting a more safe environment to achieve the control or the elimination of diseases caused by phytopathogenic fungi.

Finally, the present invention provides a composition that contains said bacterial strain in a suitable form and quantity for its biological activity. The mixture contains non toxic agents that enable to the bacteria to be adhered to the vegetable to which they are inoculated, vegetable nutrients and preservation agents, the mixture being presented as a liquid suspension or as a lyophilization obtained powder.

BACKGROUND OF THE INVENTION

The diseases caused by phytopathogenic fungi are considered as the most harmful and of larger propagation at a world level. Nowadays the control of these diseases is based fundamentally in the use of chemical fungicides that despite their high toxicity, both for plants and humans that manipulate them and/or that work in fumigated fields, and their scarce biodegradation, continue to be massively used due to their relatively efficient activity against fungal diseases, in addition to the lack of efficient and environmentally more safer alternatives.

*Botrytis cinerea* is a phytopathogenic fungi that infects a great number of economically important vegetable species, including fruit trees, decorative plants and vegetables. This fungi produces a disease known as grey rot, resulting in a mayor problem both pre and post-harvest of strawberries, raspberries, apples, pears, chestnuts, kiwis and grapes, among others. In the grapevine this fungus produces the grape bunch rot, a disease that is currently considered as one of the most serious at a production level in the fruit export market in Chile, as it can cause great losses not only in the fields but also during storage and shipping (van Kan J. A. 2006. Licensed to kill: the lifestyle of a necrotrophic plant pathogen, Trends Plant Sci. 11, 247-253; Elad, Y., Williamson, B., Tudzynski, P. and Delen, N. eds. 2007. *Botrytis:* Biology, Pathology and Control. The Netherlands: Kluwer Academic Publishers).

Today the control of this important phytopathogen is mainly carried out by chemical fungicides. However, in the last years some microorganisms having anti-fungal activity against *B. cinerea* have been described. Some of the most promissory examples is Serenade®, which active principle is a bacteria known as *Bacillus subtilis* QST 713, discovered in soil samples of a vegetable garden by the AgraQuest Inc. enterprise in Davis, Calif. This biofungicide is registered in various countries, including Chile. It has a low toxicity, and it is being commercially used in the United States for the control of diseases such as oidium (*Uncinula necator*), grey rot caused by *Botrytis cinerea* and acid rot in grapevines.

U.S. Pat. No. 5,869,038 describes bacterial isolates of the *Pseudomonas fluorescens*, *Serratia liquefaciens*, *Serratia plymuthica*, *Bacillus subtilis*, *Bacillus pumilis* and *Bacillus polymyxa* species, that are effective in inhibiting the development of *Botrytis cinerea* and *Alternaria brassicicola*, fungi that causes post-harvest diseases in cabbages. The *Serratia plymuthica* bacteria described in this patent corresponds to the strain CL43, different from the bacterial strain in the present invention, and conveniently used in mixtures with the previously mentioned bacteria in order to inhibit the fungus development with a suitable efficiency. On the contrary, the bacterial strain CCGG2742 as a pure culture efficiently inhibits *B. cinerea* and it is not necessary to mix it with other bacteria in order to use it as a biofungicide.

U.S. Pat. No. 6,004,774 discloses a *Bacillus subtilis* strain to inhibit the development of pathogenic plant fungus and bacteria, and describes methods to treat or protect plants from infections with fungus and bacteria.

U.S. Pat. No. 6,077,506 refers to a novel *Bacillus thuringiensis* bacterial strain that presents a wide anti-fungal and anti-bacterial capacity. Furthermore, the use of the *bacillus thuringiensis* bacterial strain or the antibiotic that it produces for the control of a wide range of plant pathogenic bacteria and fungus is described.

Publication WO 00/57706 discloses a substantially pure biological culture of a *Pantoea agglomerans* bacterial strain, its use as antagonist for the biological control of fungi responsible for the fruit rot. A very high efficacy resulted from such antagonist and it is comparable to those synthetic fungicides that are of most use. The antagonist is effective to fight the rot caused by *Botrytis cinerea*, *Penicillium digitatum*, *Penicillium expansum*, *Penicillium italicum* and *Rhizopus stolonifer*.

Publication WO 02/072795 discloses a group of bacteria that are antagonists for the protection against plants phytopathogenic fungi and bacteria. The isolated bacteria are the *Paenibacillus polymyxa*, *Pseudomonas chlororaphis*, *Pseudomonas putida*, *Serratia plymuthica* and *Bacillus subtilis* species. In this case, the bacterial strain *Serratia plymuthica* VKPM B-7957 is also different from the bacterial strain of the present invention, because when used in a pure culture, the efficacy of this bacteria against phytopathogenic fungus is very low, and it must be used in mixtures with other bacteria that have fungicide activity to boost its effect.

Publication WO 03/000051 discloses a biologically pure culture of a microorganism, *Bacillus licheniformis*, bacterial strain SB3086, to be used as a biofungicide.

The application of living organisms as biological control agents presents some limitations such as a narrow effective range against vegetable pathogens, and instability in time, resulting in a short permanence of the living organism in the environment and therefore a very low biopesticide action efficacy. Many of the bacterial strains used die within some weeks when subjected to standard storing conditions, or within hours in the typical conditions faced in the field, with relatively high temperatures and the deleterious effects of UV light on the actively growing microorganism. The attempts to grow said microorganisms in the same place where they should be used have been of some usefulness. However, the serious problems of culture contamination and the need of the biocontrol agent to be applied late in the day in order to prevent the effects of UV light and temperature make the system complicated and the process expensive.

This explains that for the time being an effective and environmentally friendly biological control method, that enables to inhibit the damage on plants originated by fungal diseases, has not been yet designed, thus constituting a great challenge to the scientists, and a great necessity to the agricultural industry, in order to diminish the use of synthetic chemical fungicides that currently are of massive use.

Therefore it is an object of this invention to provide an efficient, environmentally safe biological agent with biofungicide activity, for controlling plant's diseases caused by phytopathogenic fungus and microorganisms, in particular *B. cinerea*.

FIGURE DESCRIPTION

FIG. 7 shows the partial nucleotide sequence of the 16S rDNA of *S. plymuthica* CCGG2742

FIG. 8 shows the effect of the bacteria as a biocontrol in fruits incubated at 20° C.

DETAILED DESCRIPTION OF THE INVENTION

Figure 1:
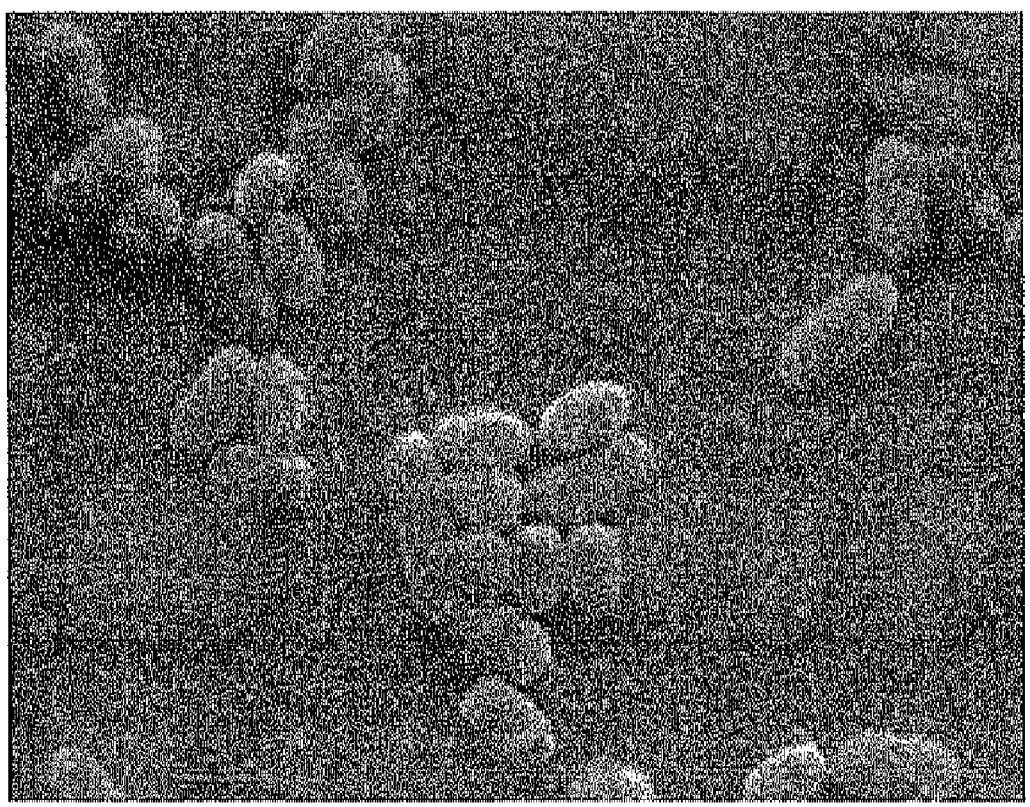
FIG. 1 is a scanning electronic microphotography of *Serratia plymuthica* CCGG2742 cells. The bar in the left lower corner represents 1 μm.

The bacterial strain CCGG2742 corresponds to the *Serratia plymuthica* species. Its characterization by means of microbiological and biochemical assays is shown in Tables 1, and 3. It produces uncoloured/white colonies without pigmentation in agar *Luria Bertani* (LB) and in agar supplemented with malt extract (20 g/L).

TABLE 1

Morphologic and physiological characteristics of *Serratia plymuthica* CCGG2742.

| Form | Bacillus |
|---|---|
| Gram's strain | Negative |
| Motility | + |
| Pigment production | − |
| Growth at 4° C. | + |

TABLE 2

Biochemical tests for the characterisation of *Serratia plymuthica* CCGG2742.

Biochemical tests

| Test | | Test | |
|---|---|---|---|
| Indol production (IND) | − | Ornithin decarboxylase (ODC) | − |
| Tryptophan deaminase (TDA) | − | Lipase (LIP) | − |
| Voges-Proskauer reaction (VP) | + | Esculin hydrolysis (ESC) | + |
| DNase | + | Gelatine hydrolysis (GEL) | + |
| Catalase | + | $H_2S$ production (H2S) | − |
| Malonate use (MAL) | − | $NO_3$ production (NO3) | + |
| Citrate use (CIT) | + | $N_2$ production (N2) | − |
| Sorbitol use (SBL) | + | β-Glucoronidase (GUR) | − |
| Aliphatic thiols use (TET) | + | Galactosidase (ONPG) | + |
| Urease (URE) | − | β-Xylosidase (B-Xil) | − |
| Oxidase | − | β-Glucosidase | + |
| Arginin dehydrolase (ADH) | − | N-Acetil-β-D-glucosaminidase (NAG) | + |
| Lysine decarboxylase (LDC) | − | Pyrronilodyl aminopeptidase (PYR) | − |

In brackets is the name by which the test is known, and then the result of the test is indicated positive (+) or negative (−).

TABLE 3

Fermentation of carbohydrates by *Serratia plymuthica* CCGG2742.

| Polyols fermentation | | Carbohydrates fermentation | |
|---|---|---|---|
| Adonitol (ADON) | − | L-Sorbose (SBE) | − |
| Mannitol (MAN) | + | Dulcitol (DUL) | + |
| Inositol (INO) | − | Inuline (INU) | + |
| Sorbitol (SOR) | + | Methyl-α-D-manopyranoside (MDM) | + |
| Glycerol (GLY) | + | Methyl-α-D-glucopiranoside (MDG) | − |
| Erythritol (ERY) | − | Arbutine (ARB) | + |
| Xylitol (XLT) | − | Salicine (SAL) | + |
| D-Arabitol (DARL) | − | D-Cellobiose (CEL) | + |
| L-Arabitol (LARL) | − | D-Maltose (MAL) | + |
| Carbohydrates fermentation | | D-Lactose (LAC) | + |
| L-Rhamnose (RHA) | − | D-Trehalose (TRE) | + |
| D-Saccharose (SAC) | + | D-Melezitose (MLZ) | + |
| D-Melibiose (MEL) | + | D-Raffinose (RAF) | − |
| Amygdaline (AMY) | + | Starch (AMD) | + |
| L-Arabinose (DARA) | + | Glycogen (GLYG) | − |
| D-Arabinose (LARA) | − | Gentibiose (GEN) | + |
| D-Ribose (RIB) | + | D-Turanose (TUR) | − |
| D-Xylose (DXYL) | + | D-Lyxose (LYX) | − |
| L-Xylose (LXYL) | − | D-Tagatose (TAG) | + |
| Metil-β-D-xylopyranoside (MDX) | − | D-Fucose (DFUC) | − |
| D-Galactose (GAL) | + | L-Fucose (LFUC) | − |
| D-Fructose (FRU) | + | Potassium gluconate (GNT) | − |
| D-Glucose (GLU) | + | Potassium 2-gluconate (2 KG) | − |
| D-Mannose (MNE) | + | Potassium 5-gluconate (5 KG) | − |

The positive (+) and negative (−) reactions are indicated. Furthermore, the abbreviation used for every test is indicated in parenthesis.

Furthermore, the susceptibility of *Serratia plymuthica* CCGG2742 to various antibiotics is established, the results being presented in Table 4, wherein the antibiotic essayed and its concentration are indicated, and wherein they are classified according to the family to which they belong.

TABLE 4

Susceptibility of *Serratia plymuthica* CCGG2742 to various antibiotics.

| Fluoroquinolones | |
|---|---|
| Ciprofloxacin 5 µg | S |
| Cephalosporines | |
| Ceftriaxone 30 µg | S |
| Cefoperazone 75 µg | S |
| Ceftazidime 30 µg | S |
| Cefotaxime 30 µg | S |
| Cefazolin 30 µg | R |
| Cefadroxil 30 µg | R |
| Cefuroxime 30 µg | R |
| Cefalotin 30 µg | R |
| Penicillines | |
| Penicillin 10 U | R |
| Oxacillin 1 µg | R |
| Ampicillin 10 µg | R |
| Carbenicillin 100 µg | S |
| Amino-pencillines | |
| Amoxicillin 25 µg | R |
| Monobactames | |
| Aztreonam 30 µg | S |
| Lincosamides | |
| Clindamycin 2 µg | R |
| Macrolides | |
| Erythromycin 15 µg | R |
| Aminoglycosides | |
| Gentamicin 10 µg | S |
| Amikacine 30 µg | S |
| Nitrofurans | |
| Nitrofurantoin 300 µg | R |
| Phenicols | |
| Chloramphenicol 30 µg | S |
| Glycopeptides | |
| Vancomycin 30 µg | R |
| Polypeptides | |
| Bacitracin 10 U | R |
| Amino-coumarines | |
| Novobiocin 5 µg | R |
| Others | |
| Sulfa trimethropim 25 µg | S |
| Tetracycline 30 µg | R |
| Sulbactam-Ampicillin 10/10 µg | R |

The sensibility (S) or resistance (R) to each one of the antibiotics is indicated.

Figure 2:
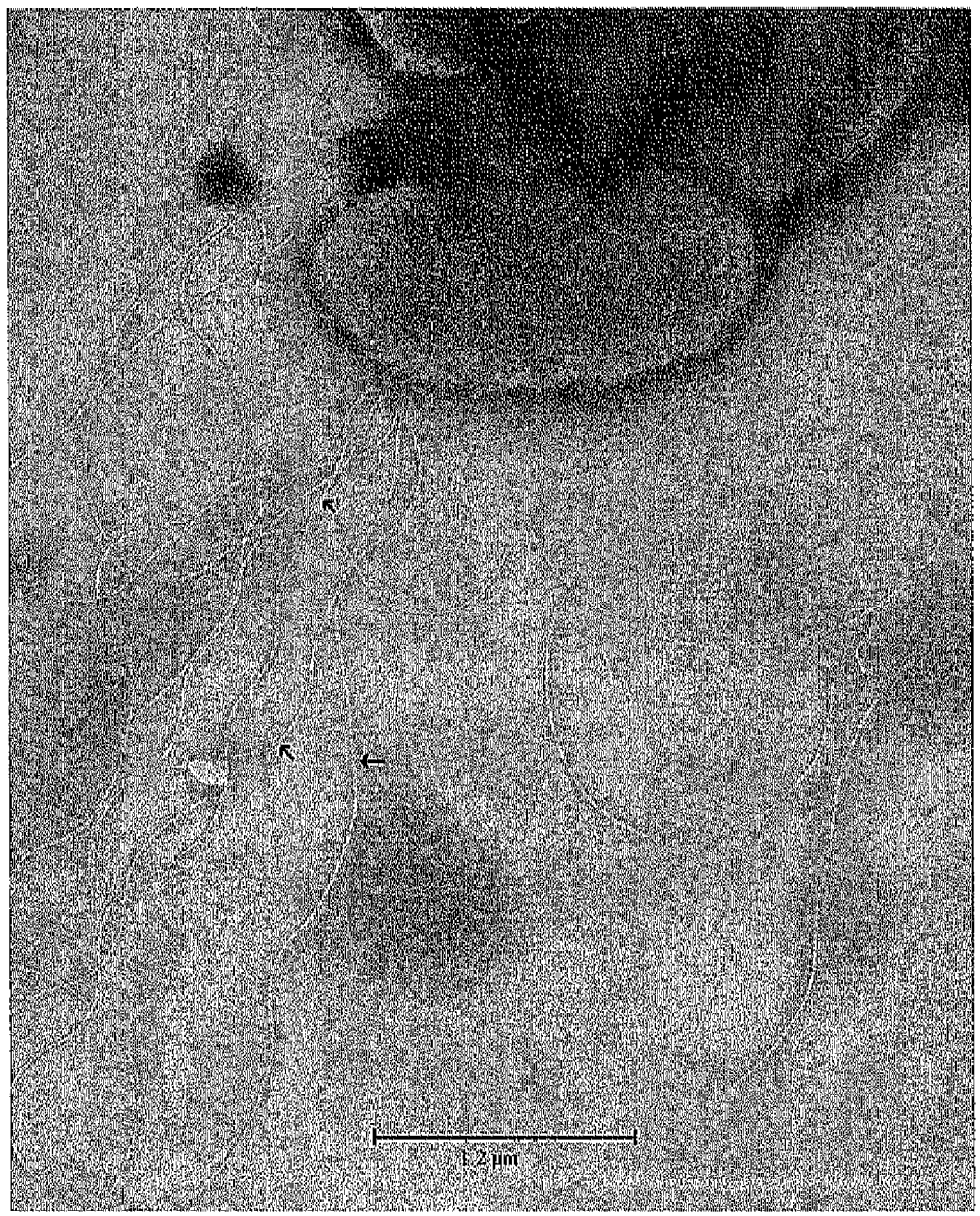
FIG. 2 is a microphotography of *Serratia plymuthica* CCGG2742. Negative stain with 1% potassium phosphotungstate.
Figure 3:
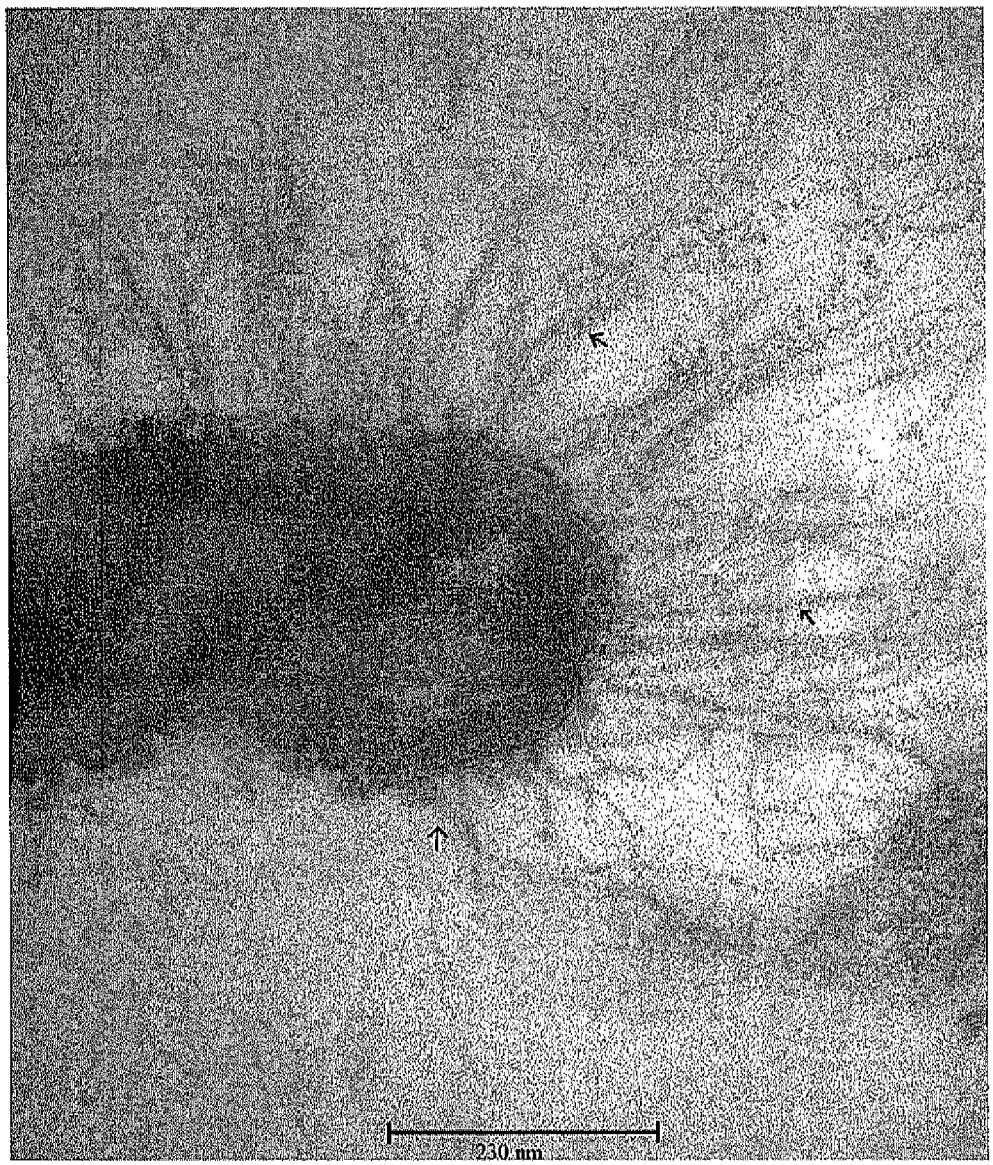
FIG. 3 is a microphotography on ultrathin slices of *Serratia plymuthica* CCGG2742

At an optic microscopy level, the cultures are comprised of mobile negative Gram bacillus, whereas at a scanning electron microscopy level the bacillus morphology is clearly observed with a length size in the range of 0.7-1.5 µm and a width size in the range of 0.6-0.8 µm (FIG. 1). The scanning electron microscopy analysis does not allow to detect the presence of bacterial appendices. However, using the negative stain technique and ultrathin slices of the bacteria, the presence of peritrichous flagella (FIGS. 2 and 3) has been detected, under transmission electron microscopy, perfectly matching the mobility tests.

The optimal growth temperature range was established for the bacterial strain, range that runs between 4° C. and 37° C., growth not occurring above the indicated temperature. The visual representation of this result can be observed in FIG. 4, wherein the growth of the bacteria, measured as $DO_{600nm}$ is represented at 12 hours from the incubation at each condition. The growth temperature range is quite broad, a very important experimental information, since the bacterium can be used as a biofungicide for the pre-harvest of fruits in a period wherein the temperatures at the field can range from very low in winter to very high in summer. Furthermore, during post-harvest the fruit is generally stored in cold and some phytopathogenic fungus like *B. cinerea* can grow at low temperatures and so in this storing conditions the fruit decays. Therefore it is of vital importance that the bacteria can grow at low temperatures in order to broaden the range of this parameter and be able to use it as a post-harvest biofungicide.

Figure 5:
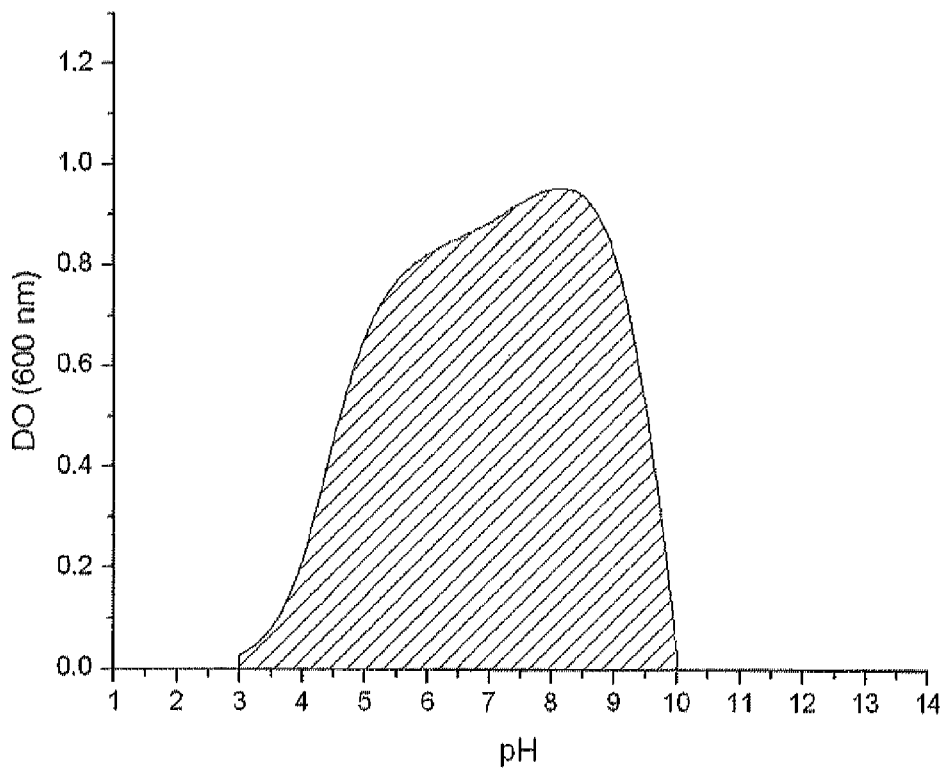
FIG. 5 depicts a graphic of the growth of *Serratia plymuthica* CCGG2742 in culture media buffered at different pH values.

Even more, the bacteria is capable of growing in a broad pH range (FIG. 5), which is also another positive quality, thus providing greater versatility when used as a biofungicide. For the determination of the pH effect over the bacterial growth, growth curves in culture media adjusted at various different pH values were performed. In FIG. 5 the growth at 12 hours from the incubation of the bacterial strain is shown against different concentrations of protons present in the media. It was established that the range of pH for the optimal bacterial growth is between 4 and 9 pH units, both values included.

Figure 6:
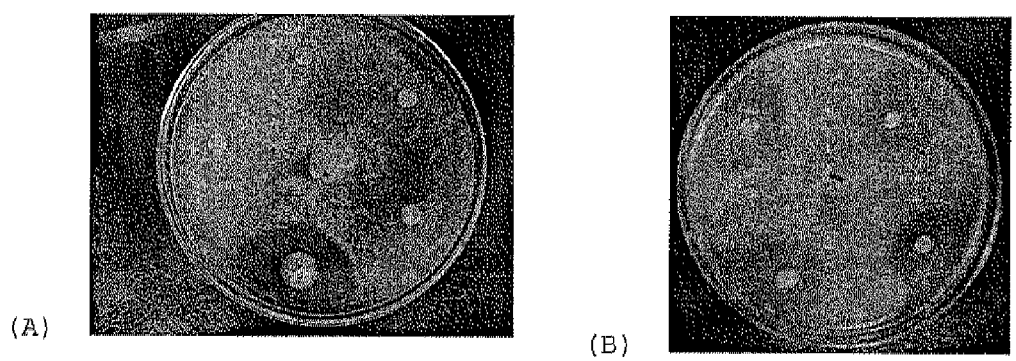
FIG. 6 shows the effect of biofungicide bacteria over *Botrytis cinerea* mycelium.

The opposing effect of *S. plymuthica* CCGG2742 against *B. cinerea* is shown in FIG. 6. In (A) and (B) the inhibition halo produced by the fungitoxic molecules released by the bacteria, that diffuse in the agar, preventing the fungus development is observed. In (A) sensidisks without active principles are used as negative controls.

Further to the microbiological and biochemical characterization of the bacteria, its molecular characterization was carried out by means of the determination of the nucleotide sequence of the 16S rDNA and its bioinformatics analysis. In FIG. 7 the partial nucleotide sequence of the 16S rDNA is presented for *S. plymuthica* CCGG2742 (994 nucleotides). The alignment of this sequence with existing sequences in data bases using Blast results on the following:

described hereinafter are suitable for the fast growth of the bacterial cells and to help the secretion of the fungitoxic molecules:
  i) Malt extract 20 g/L
  ii) LB media (*Luria Bertani*). This media contains yeast extract (5 g/L), tryptone (10 g/L) and NaCl (10 g/L). The pH must be adjusted to 7.5.

In any of these culture media, after the addition of the bacterial inoculum, the incubation is carried out at 20° C. for a minimal time of 12 hours. For solid media 15 g/L of agar-agar is added.

Establishment of Deleterious or Pathogenic Effects on Plants and Fruits

According to the experimental results obtained, *S. plymuthica* CCGG2742 does not show pathogenic effects on leaves of plants (bean and grapevine) nor fruits (grapes).

The experimental procedure was the following: 10 μL of the bacterial culture grown in LB at different dilutions (from approximately $1 \times 10^6$ cfu/mL up to $2 \times 10^{12}$ cfu/mL) are inoculated as a drop over the skin of untouched grapes (without damage). Also, on another grape berries, the same volume was inoculated (10 μL) of the same culture dilutions, but by means of a puncture through the fruit's skin (bacterial injection). The observation of the grape berries 7 days after inoculation did not reveal any type of external nor internal change of the fruit inoculated with living bacteria. These experiments were carried out in triplicate with white and pink grape berries. As a control grape berries were inoculated under the same described conditions but instead of inoculating with bacteria, they were inoculated with 10 μL of sterile LB culture media. During the whole incubation at 20° C., the fruit was maintained in a glass dish with agar at 1.5% in order to maintain the humidity.

Establishment of the Temperature and pH Conditions for the Optimal Growth of *S. plymuthica* CCGG2742

The establishment of the growth temperature range of the bacterial strain was carried out in malt extract media (ME;

TABLE 5

Results of the alignment of 16S rDNA of *Serratia plymuthica* CCGG2742 in BlastN.

| Accession code | Description | Maximal score | Total score | Query coverage | E value | Maximal identity |
|---|---|---|---|---|---|---|
| DQ365586 | Partial sequence of the ribosomal ARN 16S genome of *Serratia plymuthica* strain GS10 | 1118 | 1118 | 65% | 0.0 | 97% |

The values of the parameters computed by the software are indicated.

Therefore, the microbiological, biochemical, electron microscopy, and 16S rDNA sequencing test confirmed that it is a new bacterial strain of *Serratia plymuthica*, isolated from the skin of grapes collected in Chile and that we denominated CCGG2742.

EXPERIMENTAL SECTION

Procedures for the Propagation of the New Bacterial Strain *Serratia plymuthica* CCGG2742

Figure 4:
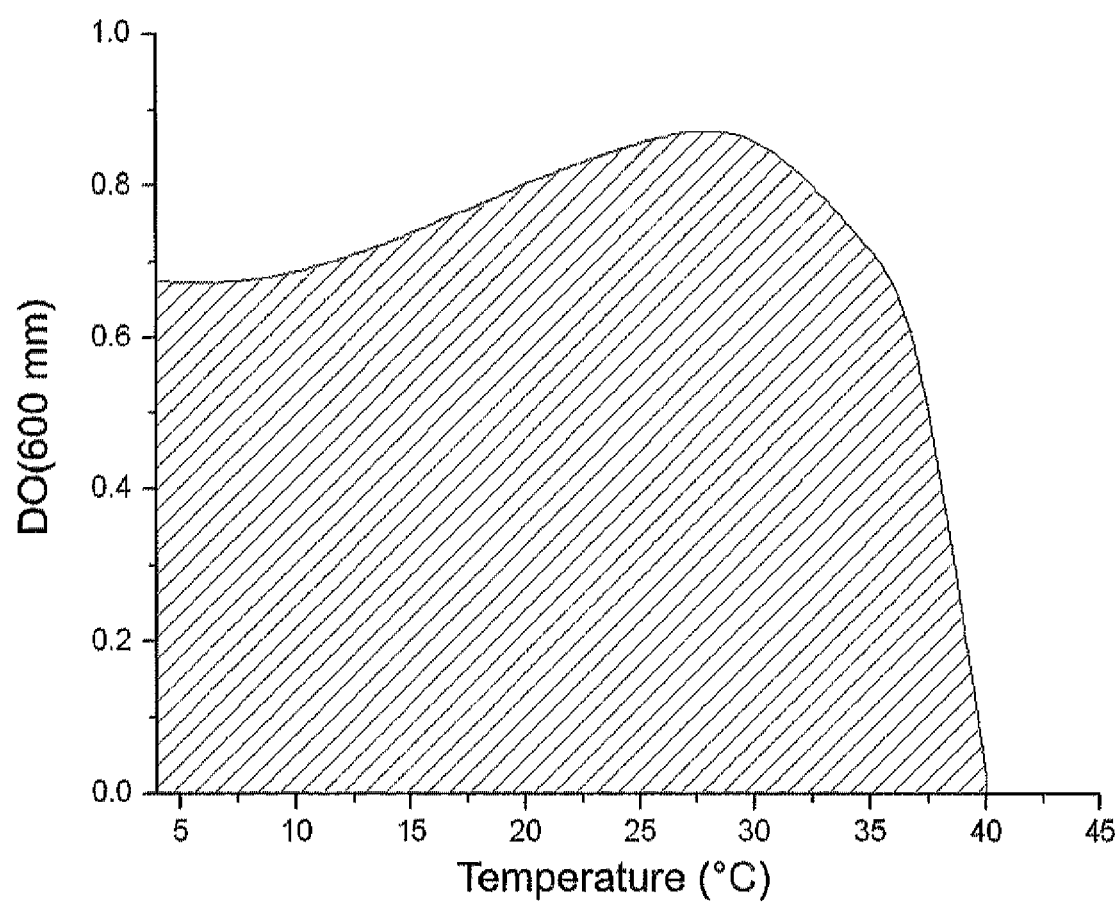
FIG. 4 depicts a graphic of the growth of *Serratia plymuthica* CCGG2742 at different temperatures.

The propagation of the bacteria can be carried out both in solid and liquid culture media. The following culture media malt extract 20 g/L, Peptone 1 g/L), at the following temperatures: 4, 10, 20, 25, 30, 35, 37 and 40° C. (FIG. 4). One mL of the bacterial inoculum from a culture grown for 16 h, with an optical density at 600 nm ($DO_{600nm}$) of 0.8, was inoculated in a Nefelo Erlenmeyer flask that contains 50 mL of ME, and that was maintained under constant agitation (200 rpm). The $DO_{600nm}$ was recorded over time, 0-12 h with recording every 1 h, and also at 24, 48 and 72 h, for every one of the temperatures at which the experiment was carried out. The $DO_{600nm}$ is measured with an spectrophotometer (Spectronic 20, Bausch & Lomb). The determination of the pH range in which the bacterial strains grows was carried out at 30° C., using the same methodology that the one used for the determination of the temperature ranges, with the exception that, for the preparation of the ME culture media, a buffer solution was used instead of distilled water. For pHs 3, 4, 5 and 7 a phosphate-citrate buffer was used, for pH 9 a Tris-Hcl buffer and for pH 10 a glycine-NaOH buffer was used (FIG. 5) (Gomori G. 1955. Preparation of buffers for use in enzyme studies. In: Methods in Enzymology. Colowick S., Kaplan N., Eds. 1:138-146). The result of the measure of growth at 12 h was used for making a graphic representation of the temperature and pH range in which there is bacterial growth. Each one of the growth curves was carried out in triplicate.

Bioassays of Inhibition of Growth of the Mycelia

The bacterial strains of B. cinerea Bc149 and Bc55L used in the bioassays belonged to the Fungus Virology laboratory—USACH (Laboratorio de Virologia de Hongos—USACH), and were isolated from grapes. These bacterial strains were maintained in agar potato-dextrose (PDA; Oxoid) until the bioassays were carried out.

The bioassays of inhibition of growth of mycelia were carried out in agar malt extract (MEA; malt extract 20 g/L; peptone 1 g/L; agar 15 g/L) supplemented with 2% glycerol. A piece of mycelium of a diameter of 7 mm of B. cinerea Bc149 was taken and seeded in the center of the Petri dish. The bacteria was inoculated in one end (FIG. 6A) or in four different places at a distance of 4 cm from the center of the dish (FIG. 6B). The inoculum contained approximately $1 \times 10^6$ of total cfu of the bacterial strain. The growth was observed during 7 days at 20° C. As a control, the same experiment was carried out but without the inoculation of the bacterial strain. These assays were carried out in triplicate.

Biofungicide Effect of the *Serratia plymuthica* Bacterial Strain

Bean and grapevine leaves were inoculated with $10^5$-$10^8$ cfu/mL. They were incubated at 20° C. for 12 hours and then the phytopathogenic fungus was sprayed on the plant using conidia concentrated suspensions ($10^4$-$10^6$ conidia). They were incubated for 4-8 days and the degree of infection or the damage produced in the plant were established, comparing it with a control to which spores of the phytopathogenic fungus were not added and with leaves that were not inoculated with the bacteria. The experiment was carried out in triplicate. An efficient an suitable protection was observed when the bacteria was applied in a preventive way. It was also effective when applied simultaneously with the pathogen, 0, 12 or 24 hours after the addition of the pathogen on the plant.

In order to evaluate the effect of the bacteria as a biocontrol agent when used directly on fruit, Thompson Seedless variety grape bunches were used, that were harvested in Colina, Metropolitan Region, Santiago, Chile. The grape bunches did not receive a post-harvest treatment and weighted 500-620 g. According to the experimental conditions detailed in Table 6, the bunches used under experimental conditions 1 and 2 were inoculated directly. The bunches used under experimental conditions 3 to 9 and in the control were washed once with a 0.5% solution of sodium hypochlorite, then three times with sterile distilled water and were left to dry in a sterile environment. Then, each bunch was stored in a plastic box, and the respective treatment was applied in accordance with the experimental condition.

TABLE 6

Treatments applied to grape bunches in each experimental condition.

| Experimental condition | Suspension or inoculated media, 0 h (5 mL) | Suspension or inoculated media, 24 h* (5 mL) |
| --- | --- | --- |
| 1 | $5 \times 10^8$ cfu | $5 \times 10^4$ conidia |
| 2 | $5 \times 10^4$ conidia | $H_2O$ sterile |
| 3 | $5 \times 10^6$ cfu | $H_2O$ sterile |
| 4 | $5 \times 10^8$ cfu | $H_2O$ sterile |
| 5 | $5 \times 10^4$ conidia | $H_2O$ sterile |
| 6 | $5 \times 10^4$ conidia | $5 \times 10^6$ cfu |
| 7 | $5 \times 10^4$ conidia | $5 \times 10^8$ cfu |
| 8 | $5 \times 10^6$ cfu | $5 \times 10^4$ conidia |
| 9 | $5 \times 10^8$ cfu | $5 \times 10^4$ conidia |
| Control | $H_2O$ sterile | $H_2O$ sterile |

The total cfu of *S. plymuthica* CCGG2742 or total conidia of *B. cinerea* Bc55L present on the bunches is detailed according to each experimental condition.
*Corresponds to the treatment that was inoculated 24 h after the treatment inoculated at 0 h.

Figure 8:
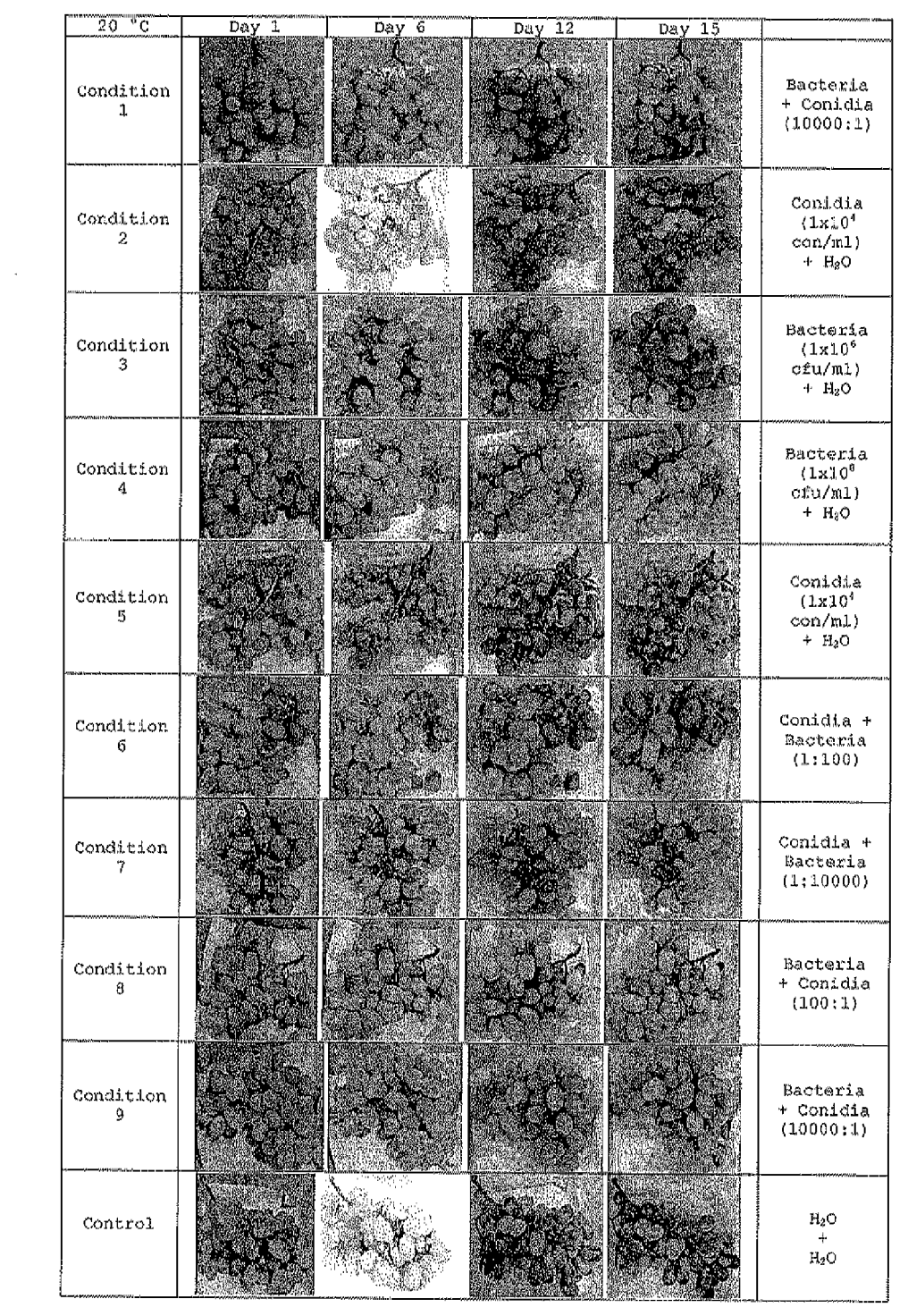
Figure 9:
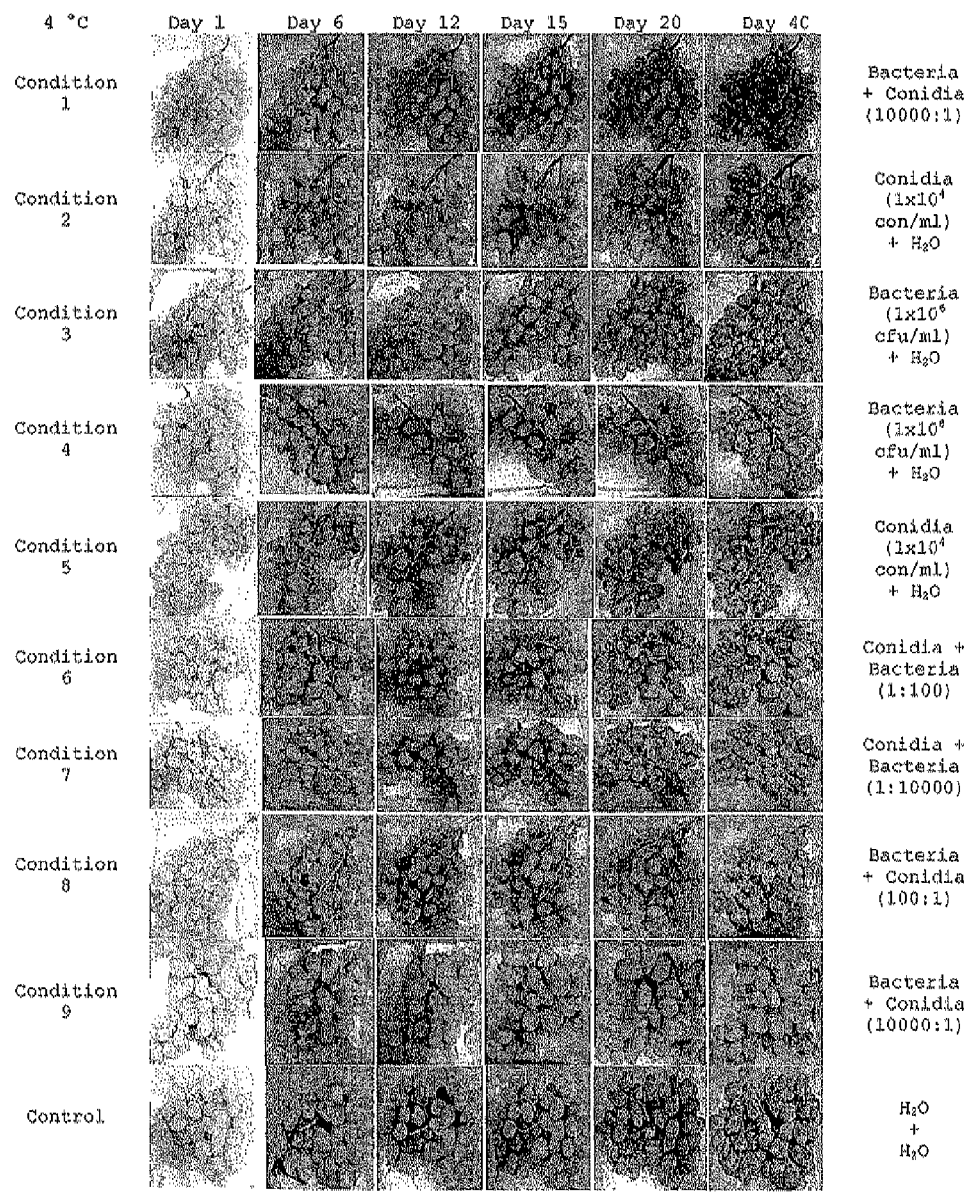
FIG. 9 shows the effect of the bacteria as a biocontrol in fruits incubated at 4° C.

This experiment was carried out at two temperatures: 20° C. (FIG. 8), wherein the development of the pathogen was observed for 15 days; and 4° C. (FIG. 9), wherein the development of the pathogen was is observed for 40 days. Each experimental condition was carried out in triplicate. In both temperature conditions, the bacterial strain CCGG2742 efficiently protects the fruit against the infection produced by *B. cinerea*. This is another important difference with the CL43 bacterial strain described in U.S. Pat. No. 5,869,038. The antifungal efficacy of the CL43 bacterial strain notably drops when the experiments are carried out at 4° C.

Both the application of the spores and the application of the bacterial cells must be carried out using an oily solvent that enables the adhesion of the conidia and bacteria to the plant. It must be resuspended in an aqueous solution containing Pelgel 0.5% (Liphatech, Milwaukee, Wis.) as an adhesive component. Pelgel is a mixture of carboxymethyl cellulose with Arabic gum. Further to providing adhesion characteristics to the conidia and to the bacteria, it allows its adherence to the plant surface and it is useful as a nutrient.

Storing and Maintaining the Bacterial Biofungicide

The bacterial strain CCGG2742 can be maintained indefinitely in the laboratory using general bacteriology techniques. The short term conservation (1-3 months) is obtained by seeding the bacteria in tubes with slant nutritive agar, maintaining the tubes in the refrigerator at 4° C. For maintaining the bacteria for a 6 months to 1 year delay, it is necessary to freeze concentrated suspensions of the bacteria in glycerol 30-50% (v/v) at −80° C. Finally, if the bacteria is to be stored for longer periods of time, it is necessary to use the lyophilization technique. The cultures of this bacteria are fully treatable by lyophilization and the lyophilizates can be maintained in a very stable form for at least 1 year at room temperature.

The invention claimed is:

1. Isolated *Serratia plymuthica* strain CCGG2742, designated 7404 via CECT.

2. A biofungicide composition comprising the isolated strain of claim 1 and an agriculturally acceptable carrier.

3. A method for controlling a phytopathogenic fungal infection comprising applying an effective amount of the composition of claim 2 to a plant or fruit.

4. The method of claim 3, wherein said phytopathogenic fungal infection is caused by a *Botrytis* fungus.

5. The method of claim 4, wherein said *Botrytis* is *Botrytis cinerea*.

6. The method of claim 3, wherein said effective amount ranges from $10^5$-$10^8$ cfus/ml.

7. The method of claim 3, comprising applying said composition to fruit prior to harvest thereof.

8. The method of claim 3, comprising applying said composition to fruit after harvest thereof.

9. A method for preventing fruit rot, comprising aspersing fruit with the composition of claim 2.

10. The method of claim 9, comprising aspersing said composition in liquid form, or in an aqueous suspension of a lyophilized powder.

* * * * *

SEQUENCE LISTING

<160> NUMBER OF SEQ ID NOS: 1

<210> SEQ ID NO 1
<211> LENGTH: 994
<212> TYPE: DNA
<213> ORGANISM: S. plymuthica

<400> SEQUENCE: 1

```
tttttatgac gctggcggca ggcctaacac atgcaagtcg agcggtagca caggagagct      60
tgctctccgg gtgacgagcg gcggacgggt gagtaatgtc tgggaaactg cctgatggag     120
ggggataact actggaaacg gtagctaata ccgcataacg tctacggacc aaagtggggg     180
accttcgggc ctcacgccat cagatgtgcc cagatgggat tagctagtag gtggggtaat     240
ggctcaccta ggcgacgatc cctagctggt ctgagaggat gaccagccac actggaactg     300
agacacggtc cagactccta cgggaggcag cagtggggaa tattgcacaa tgggcgcaag     360
cctgatgcag ccatgccgcg tgtgtgaaga aggccttagg gttgtaaagc actttcagcg     420
aggaggaagg gttcagtgtt aatagcactg tgcattgacg ttactcgcag aagagcaccg     480
gctaactccg tgccagcagc cgcggtaata ctgatggtgc aagcgttaat cggaattact     540
gggcgtaaag cgcacgcatg cggtttgtta agtcagatgt gaaatccccg cgcttaacgt     600
gagaactgca tttgaaactg taaactagat tcttgtagag gggggtaaaa atctcagtgt     660
ttctgtcaaa gtctttcaat ctgcacttat ccctacgcat aagctgcttc tgttacaatt     720
ctgacctaca ttgtaatttc gacgtataaa cttattatta tcttggtctc tcgcgttact     780
ctagtgatta gatttgtcta ttattcttgt tctcaagtat tgtttctata tactttttat     840
cttccaatcc ttcggttacc tttatatttt attcccttct cttttcacat aactgctata     900
ttgtatttca ttttcttcat ttctttaact tcacattctt tgtcctttgt tacctctttc     960
aaaatattct tccgttaatg agttctccag tagc                                 994
```